United States Patent [19]

van Andel

[11] Patent Number: Plant 5,510

[45] Date of Patent: Jul. 9, 1985

[54] ALSTROEMERIA NAMED STALPAS

[75] Inventor: Jacob van Andel, Aalsmeer, Netherlands

[73] Assignees: B. V. Handelskwekerij; M. C. Staaveren, Aalsmeer, Netherlands

[21] Appl. No.: 521,889

[22] Filed: Aug. 10, 1983

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Chas. W. Rummler

[57] ABSTRACT

A new alstroemeria variety characterized by the unusual purple-violet coloring of its very large blossoms, the petals of which are covered with longitudinally extending pencil stripes of a darker shade of a red-purple color, and by its upright and vigorous growth habit and its more-or-less continuous production of flowers on each of its umbel arrangement of branches during each of its blooming seasons.

1 Drawing Figure

BACKGROUND OF THE NEW PLANT

This new alstroemeria originated as a seedling resulting from my crossing of plants selected from individually identified members of breeding stock maintained at Aalsmeer, Holland, for developmental purposes and this particular seedling was selected by me for propagation and test because of the overall purple-violet color of its very large blossoms which appeared to be profusely produced on strong, upright, umbel stems. I was also attracted to this plant because of its vigorous and upright growth habit and its more-or-less continuous production of flowers on each umbel branch during each of its blooming seasons. I propagated this selected plant at Aalsmeer, Holland, through several generations by root division and thereby established that the distinctive characteristics of this new plant hold true from generation to generation and appear to be firmly fixed. Propagation of this new variety is now being carried on at Aalsmeer, Holland, by dividing root stock.

DESCRIPTION OF THE DRAWINGS

This new variety of alstroemeria plant is illustrated by the accompanying photographic drawing which shows a blooming umbel of the plant with buds and flowers in various stages of opening, a portion of the view having been hand painted and the color rendition being as nearly true to the specified color as is possible to obtain.

DESCRIPTION OF THE NEW PLANT

The following is a detailed description of my new alstroemeria plant with color designations according to The R.H.S. Colour Chart of The Royal Horticultural Society of London England.

THE PLANT

Origin: Seedling.
Parentage:
- *Seed parent.*—Breeding Stock Plant No. 53.
- *Pollen parent.*—Breeding Stock Plant No. 2171-1.

Classification: Alstroemeria Hybrid.
Form: Erect bush comprising a tall, slender flowering stalk with flower bearing branches in simple umbel arrangement at its top.
Height: About 1.7 meters.

Growth: Vigorous, strong and upright.
Root stock: Tuberous.
Foliage:
- *Quantity.*—Medium.
- *Number of leaves.*—About 20 to 30 per stem.
- *Size of leaf.*—Various; depends on season.
- *Shape of leaf.*—Elliptic.
- *Texture.*—Leathery.
- *Color.*—Upper side — Dark Green. Under side — Grey Green.

THE BUD

Form: Pear shaped.
Size: Large.
- *Diameter.*—About 15 to 20 mm.
- *Length.*—About 40 to 45 mm. The six petals of this flower are a perianth, and divide simultaneously.

Peduncle:
- *Length.*—About 3 cm.
- *Character.*—The peduncle makes an angle of about 30° with the flowering stem.

THE FLOWER

Blooming habit: Continuous and profusely in early Spring and Fall.
Flower size: Very large.
- *Diameter.*—About 6.5 to 7 cm.
- *Depth.*—About 6 cm.

Borne: Singly.
- Shape: Generally funnel-like with petal tips curling outwardly.

Petalage:
- *Number of petals.*—Six.
- *Arrangement.*—Two concentric circles of three.
- *Form.*—Broad ovate.
- *Texture.*—Soft.
- *Appearance.*—Shiny.
- *Color.*—Outer petals — 80B with longitudinal patches of 80A; Inside petals — 80B with an inner portion of 155A. All petals have numerous generally longitudinally pencil stripes of 59A.

Persistence: The flowers hang on and dry.
Main stem or stalk:
- *Length.*—About 1.7 meters.
- *Color.*—Dark Green.
- *Character.*—Strong and upright.

Lasting quality of flower:

*On the plant.*—15 to 30 days.
*As a cut flower.*—10 to 15 days.

REPRODUCTIVE ORGANS

Stamens:
*Number.*—Six.
*Arrangement.*—One opposite each petal.
*Anthers.*—Size: About 8 to 10 mm. Color: Brown-Grey.
*Filaments.*—Length: About 40 mm. Color: White-Violet.
*Pollen.*—Color — Blue.
Pistils:
*Number.*—One.

*Styles.*—Length: About 10 mm. Color: Pale Violet.
*Stigma.*—Color: Pale Violet.

This plant is particularly noted for its very strong and vigorous growth habit and its continuous and profuse production of very large flowers on an unusual purple-violet color which makes an attractive addition to the alstroemeria color range.

I claim:

1. A new and distinctive alstroemeria cultivar, substantially as herein shown and described, characterized by the purple-violet coloration of its large and profusely blooming flowers which have an excellent lasting quality.

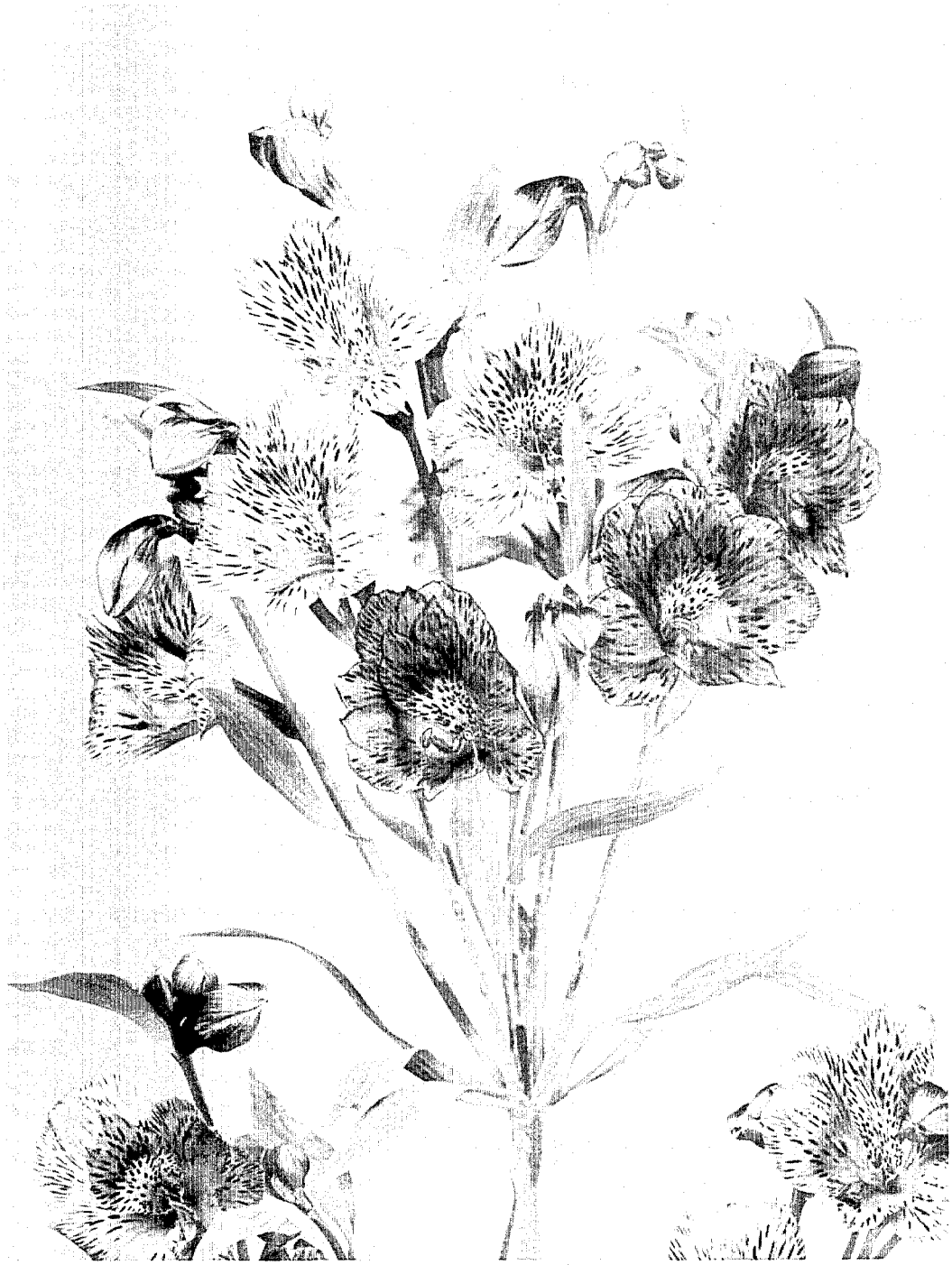

* * * * *